United States Patent [19]
Roy et al.

[11] Patent Number: 5,192,661
[45] Date of Patent: Mar. 9, 1993

[54] MULTICOMPONENT KIT CONTAINING AN ANTIBODY TO A SYNTHETIC ANTIGEN OF SIALIC ACID

[75] Inventors: Rene Roy, Gatineau; Craig A. Laferriere, Mississauga, both of Canada

[73] Assignee: University of Ottawa, Ottawa, Canada

[21] Appl. No.: 708,671

[22] Filed: May 31, 1991

Related U.S. Application Data

[62] Division of Ser. No. 81,431, Aug. 4, 1987, Pat. No. 5,034,516 issued Jul. 23, 1991.

[51] Int. Cl.[5] ................ C12Q 1/00; G01N 33/53; C07K 3/00; C07K 15/00
[52] U.S. Cl. .................... 435/7.23; 435/4; 435/7.21; 435/7.92; 435/975; 536/18.7; 530/403; 530/807; 530/389.8; 436/518; 436/531; 436/548
[58] Field of Search .............. 435/4, 7.23, 7.92, 70.21; 536/18.2, 18.7, 55.1, 55.3, 53, 4.1, 1.1, 17.2, 17.9, 22, 120; 530/807, 403, 389.8; 436/518, 531, 542, 548, 804, 813

[56] References Cited

U.S. PATENT DOCUMENTS

| 4,075,218 | 12/1991 | Jette et al. | 435/7.23 |
| 4,471,057 | 9/1984 | Kopromski et al. | 436/518 |
| 4,557,931 | 12/1985 | Irie et al. | |
| 5,034,516 | 7/1991 | Roy et al. | 536/4.1 |
| 5,079,353 | 1/1992 | Ratcliffe et al. | 536/53 |

FOREIGN PATENT DOCUMENTS

| 1083566 | 8/1980 | Canada . |
| 1105011 | 7/1981 | Canada . |
| 1111417 | 10/1981 | Canada . |
| 1111418 | 10/1981 | Canada . |
| 1194793 | 10/1985 | Canada . |
| 1198731 | 12/1985 | Canada . |
| 1203532 | 4/1986 | Canada . |
| 1206877 | 7/1986 | Canada . |
| 0098252 | 6/1983 | European Pat. Off. . |
| 0146090 | 7/1984 | European Pat. Off. . |
| 0166442 | 6/1985 | European Pat. Off. . |

OTHER PUBLICATIONS

Kosma, P., et al., Int. Carbohydrates Synp. 10-15 Aug., 1986.
Kochelkov, N. K., Pure and Appl. Chem. vol. 56(7), 923-938 (1984).
Chernyak, A. Y., et al. Carbohydrate Research, 128, 269-282 (1984).
Chernyak, A. Y., et al. Carbohydrate Research, 141, 199-212-(1985).
Roxova-Benikova, L., et al., Carbohydrate Research 122, 269-281 (1983).
Schamer, R., "Sialic Acids, Chemistry, Metabolism and Fucntion" ed. Schamer, R., Springer-Verlag, Vienna (1982).
Feizi, T., Nature, 314, 53-57 (1985).
Steward, M. W. and Howard, C. R., Immunology Today, 8,(2), 51-58 (1987).
Zanetti, M., et al., Immunology Today, 8, (1), 18-25 (1987).
Imura, H., et al., Computer Search Print Out.
Hakomori, S., Scientific American, May, 1986, p. 47.

Primary Examiner—Garnette D. Draper
Assistant Examiner—Gian P. Wang
Attorney, Agent, or Firm—Harness, Dickey & Pierce

[57] ABSTRACT

A compound X-Y wherein X comprises sialic acid, a sialic acid derivative or and oligosaccharide terminating in a sialic acid or sialic acid derivative if multibranched at the end of at least the largest branch, and, Y represents coupling means which allows an antibody to be raised to X when the compound is coupled to a carrier through the coupling nears Y and the coupled compound used to raise said antibody. These compounds show utility in that they, and antibodies raised against these, can be used in detecting and diagnosing cancers.

2 Claims, 8 Drawing Sheets

SYNTHESIS OF THE KEY PRECURSORS

MULTICOMPONENT KIT CONTAINING AN ANTIBODY TO A SYNTHETIC ANTIGEN OF SIALIC ACID

This is a division of U.S. Pat. application Ser. No. 081,431, filed Aug. 4, 1987, now U.S. Pat. No. 5,034,516, issued Jul. 23, 1991.

This invention relates to novel sialic acid and sialic acid derivative containing compounds which along with antibodies raised against them, can be used in detecting and diagnosing cancers.

Sialic acids are a group of some 30 derivatives of neuraminic acid and represent important constituents of many glycoproteins and glycolipids (gangliosides). These carbohydrates occupy a peculiar position at the penultimate non-reducing end of oligosaccharide chains and they serve as recognition sites for agglutinins, antibodies, hormones, toxins and viruses. This phenomenon is responsible for tissue-specific adherence and colonization by microorganisms. It has also been demonstrated that sialic acids mask recognition sites and this behaviour accounts for the inertness of the immune-defence system towards many sialic acid antigens. Another important role of the sialic acid is then involvement in differentiation and onco-development antigens. As such, they could constitute key functional entities in the design of oncogenic markers.

N. K. Kochetkov in Pure and Appl. Chem. 56 (7), 923-938 (1984) discusses synthesis of fragments of bacterial polysaccharides and their application in the preparation of synthetic antigens. These workers are concerned with producing antigens which mimic bacterial antigens rather than antigens associated with cancer and related types of diseases. A. Y. Chernyak et al in Carbohydr. Res. 128, 269-282 (1984) and in Carbohydr. Res. 141, 199-212 are also concerned with the production of synthetic bacterial antigens.

U.S. Pat. No. 4,557,931 (inventors R. F. Trie et al, issued Dec. 10, 1985) relates to a GM2 ganglioside present on the surface of tumors and which is capable of stimulating an appreciable immune response These inventors are concerned with the production of this GM2 ganglioside from a related and abundant, GM1 ganglioside.

R. Schauer in "Sialic Acids, Chemistry, Metabolism and Function" ed R. Schauer, Springer Verlag Vienna (1982), discusses the importance of sialic acids and their role as biological masks, for example, in protecting invading pathogens and in normal cellcell recognition e.g. of human red blood cells.

T. Feizei in Nature 314, 53-57 (1985) pointed out that many cell surface antigens are often glycoproteins and glycolipids and that this may reflect important roles for such carbohydrate structures as regulators of cell growth and differentiation.

T. Ogawa in European Patent Application 0,146,090 A2 filed on Dec. 7, 1984 discloses and claims sialyloligosaccharides useful as intermediates in the synthesis of sialylglycoconjugates. He further discloses and claims sialic acid and galactose derivatives useful in the synthesis of gangliosides in European Patent Application 0,166,442 A2 filed on Jun. 27, 1985.

C. Kolar et al in Canadian Patent 1,198,731 disclose means for producing synthetic T-antigens comprising D-galactoamine with a bridge-forming arm.

T. Miyauchi et al in Canadian Patent 1,194,793 describe means for producing fucosyl antigens and antibodies for recognising such antigens The antibodies thereby produced can be used in kits to detect cancers of the digestive tract.

K. J. Dean in Canadian Patent 1,206,877 discloses an immunoassay method and reagent for determining non-enzymically glucosylated proteins and protein fractures in biological fluids. This provides useful measures of control of blood glucose levels in, for example, diabetes.

Dahmen et al in European Patent Application 0,098,252 disclose sugars connected via spacer moieties to substrates. The spacer moieties resemble those of Kolar and Feizei, discussed above.

R. Lemieux et al in Canadian Patent 1,203,532 describe syntheses of human T-antigenic determinant and the production of related antigens and immunosorbents and R. Lemieux et al in Canadian Patent 1,083, 366 are concerned with the production of beta-glycosides for use, for example, as artificial blood group determinants.

It therefore appears that there is still a need for a means to produce sialic acid and derivatives thereof in such a form that they can be used to raise antibodies thereby allowing one to:

(a) produce synthetic antigens having sialic acid or related functionality,
(b) produce antibodies to sialic acid and related compounds,
(c) use (a) and/or (b) to detect abnormal levels of sialic acid related compounds, which abnormal levels are often associated with various types of cancer. This be used to monitor as well as diagnose cancer,
(d) use (a) and/or (b) in kits for detecting abnormal levels sialic acid, related compounds or antibodies thereto,
(e) produce pharmaceutical compositions which could be used to induce an antibody response thereby increasing resistance to cancer.

This invention seeks to achieve some of the above-mentioned ends.

According to the present invention there is provided a compound X-Y wherein X comprises sialic acid, a sialic acid derivative or an oligosaccharide terminating in a sialic acid or sialic acid derivative, if multibranched at the end of at least the largest branch, and, Y represents coupling means which allows an antibody to be raised to X when the compound is coupled to a carrier through the coupling means Y and the coupled compound used to raise said antibody.

In a preferred embodiment such a compound is coupled to a carrier which in particular embodiments comprises a peptide, a protein, a peptide derivative or a protein derivative. In another preferred embodiment the carrier may comprise a water-soluble polymer or may comprise a polysaccharide or a derivative thereof.

The coupling means Y may comprise a spacer moiety which in some preferred embodiments comprises a carbon chain containing at least one heteroatom, such as oxygen, sulphur or nitrogen. It is particularly preferred that such a spacer is olefinic, for example, an allyl group.

The sialic acid or sialic acid derivative-containing moiety may contain at least one other sugar moiety between the sialic acid and the spacer moiety. Galactose is such a sugar in one preferred embodiment.

The above-mentioned compound can be attached to a solid substrate such as a polymeric plastic, a protein, a polysaccharide or glass. The solid substrate can often serve as an ELISA plate.

According to another aspect of the present invention there is provided a process for preparing an antigen comprising sialic acid, a derivative thereof or an oligosaccharide terminating in a sialic acid or a sialic acid derivative residue, if multibranched at the end of at least the largest branch, which comprises reacting the above-referenced compound, as hapten, with a carrier protein to obtain the antigen.

According to a further aspect of the present invention there is also provided a process for preparing an antibody to sialic acid, a sialic acid derivative or to an oligosaccharide terminating in a sialic acid or a sialic acid derivative residue, if multibranched at the end of at least the largest branch, which comprises administering to a mammal the above-referenced compound, as hapten, linked to a carrier and collecting said antibody. Preferably when raising the antibody a spleen cell is isolated from said mammal, fused with a cancer cell to form a hybridoma cell and said hybridoma cell is subsequently cultivated to yield the antibody as a monoclonal antibody.

According to a further aspect of the invention there is provided a multicomponent kit for detecting an antibody to sialic acid, a derivative thereof or to an oligosaccharide terminating in an sialic acid or a sialic acid derivative residue, if multibranched at the end of at least the longest branch in a sample, which kit comprises at least first and second components which first and second components are in separate containers, said first component comprising the above mentioned compound, said second component comprising detection means for detecting a reaction between said antibody and the above-mentioned compound. Preferably either the first component or the second component is immobilized on a plate. It is further preferred that said detection means comprises ELISA, immunofluorescence or RIA.

According to another aspect of the present invention there is provided a method for detecting cancer in an animal which comprises treating a sample obtained from said animal suspected of containing an antibody to the above-mentioned compound with some of the above-mentioned compound, treating the resulting mixture with detection means for detecting a reaction between said antibody and said compound, a positive reaction indicating the presence of said cancer in said animal.

A further aspect of the invention comprises a method for diagnosing or monitoring cancer which comprises treating a sample, obtained from an organism suspected or known to have cancer, with an antibody to the above-mentioned compound and subsequently measuring the interaction between said sample and said antibody and comparing the interaction there found with that found in a control.

With the compounds of the invention it is feasible to provide a pharmaceutical composition containing the compound, as hapten, linked to a carrier together with a suitable diluent or adjuvant.

A further aspect of the invention comprises a combination of
(a) a moiety X comprising sialic acid, a sialic acid derivative or an oligosaccharide terminating in a sialic acid or a sialic acid derivative, if multibranched at the end of at least the largest branch, and
(b) a moiety $Y^1$ comprising a spacer having dimensions which, when said moiety X is coupled through said moiety $Y^1$ to a carrier allow an antibody to be raised to X, said moiety $Y^1$ being coupled to at least one of said moiety X and said carrier.

In Figures which illustrate various embodiments of the invention.

Figure 1:
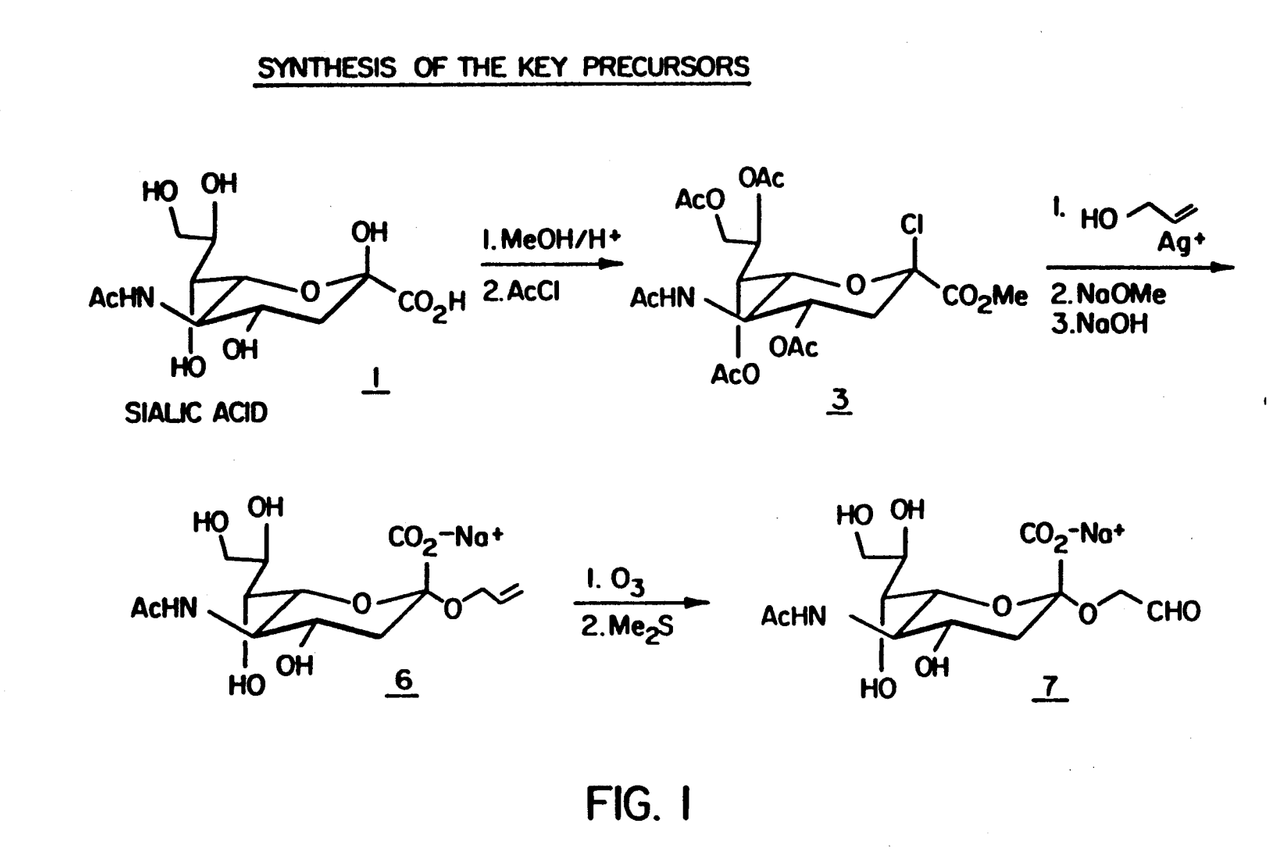
FIG. 1 shows a scheme for the synthesis of key precursors including the allyl glycoside and the aldehyde derivative.
Figure 2:
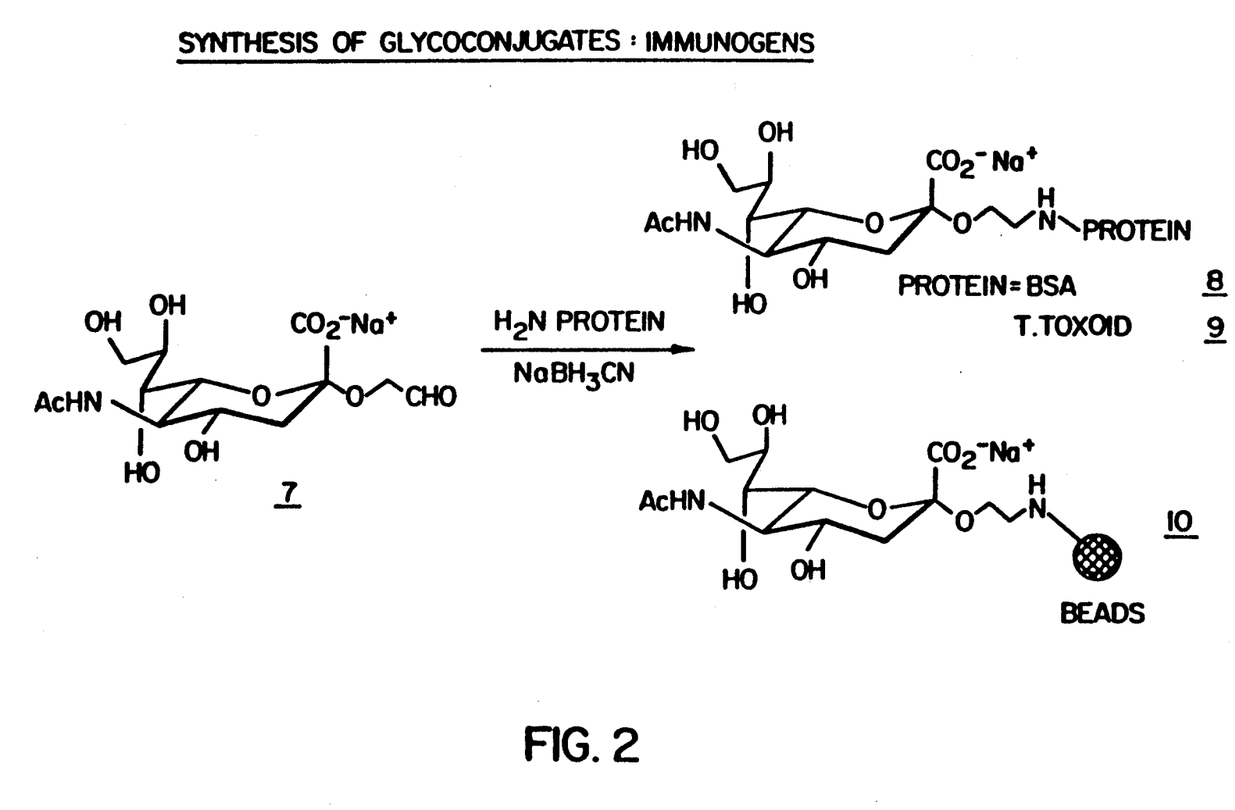
FIG. 2 shows a scheme for the attachment of an aldehyde derivative to a protein, such as bovine serum albumin or tetanus toxoid, or to beads.
Figure 3:
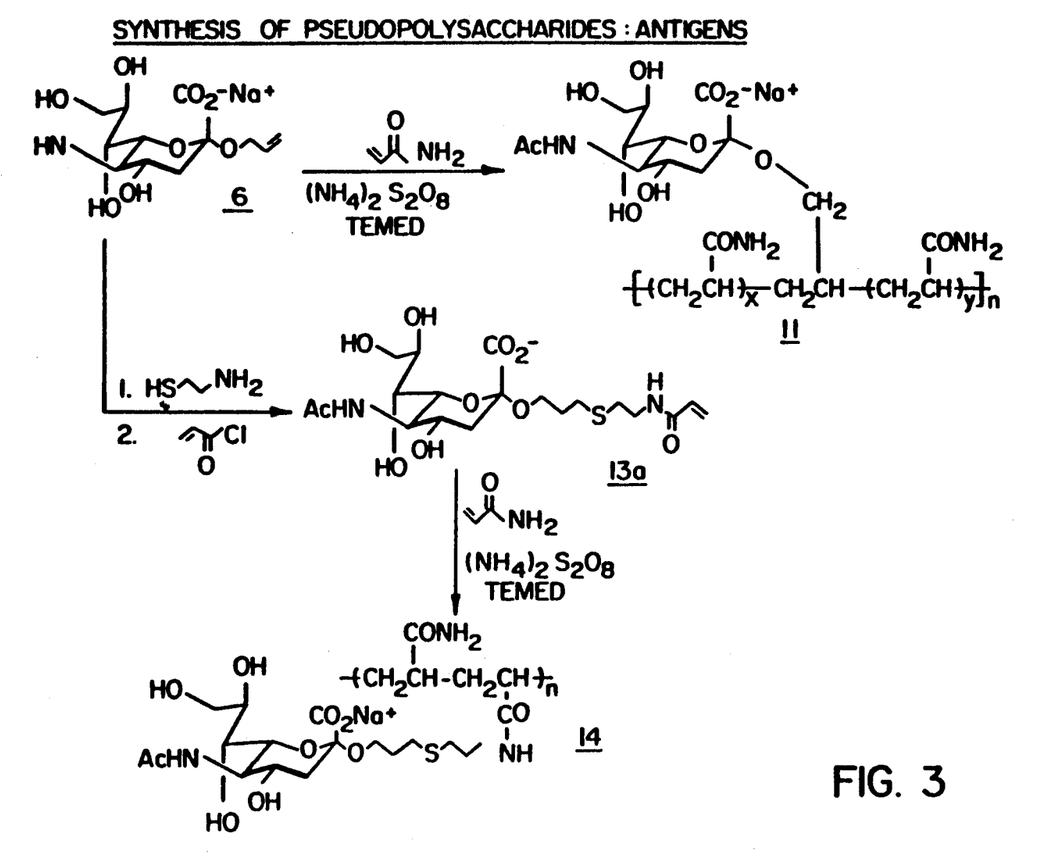
FIG. 3 shows schemes for the synthesis of pseudopolysaccharides.
Figure 4:
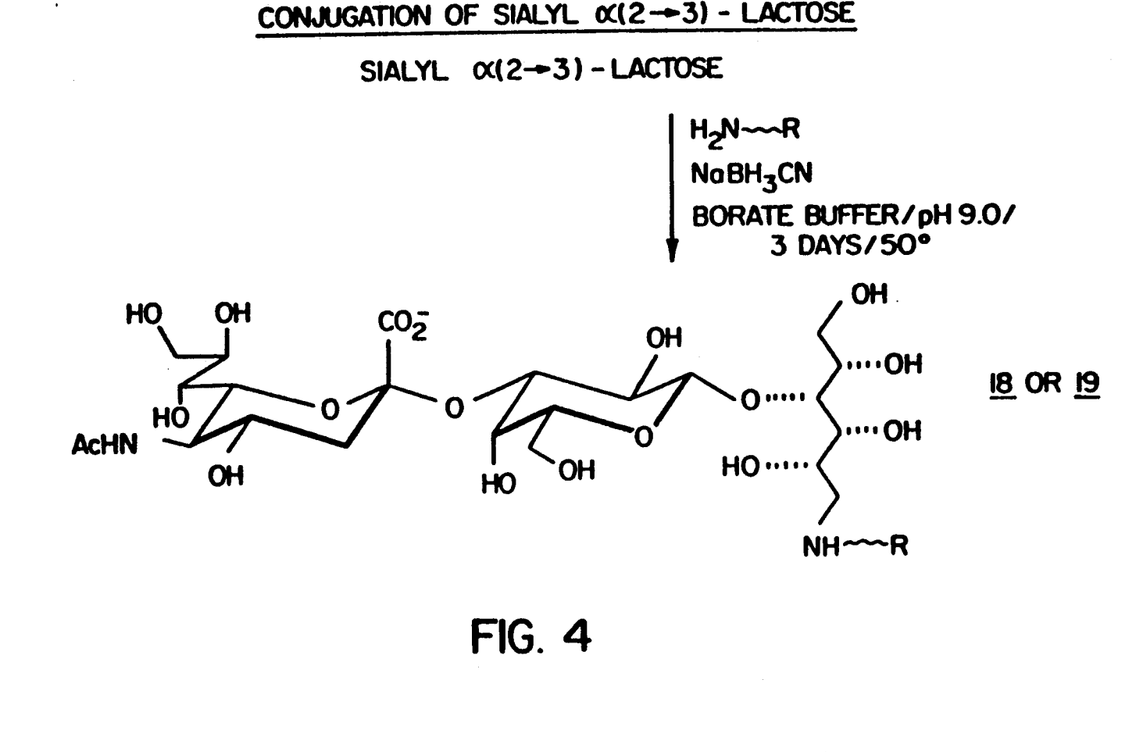
FIG. 4 shows a scheme for the conjugation of sialyl $\alpha(2\rightarrow3)$-lactose.
Figure 5:
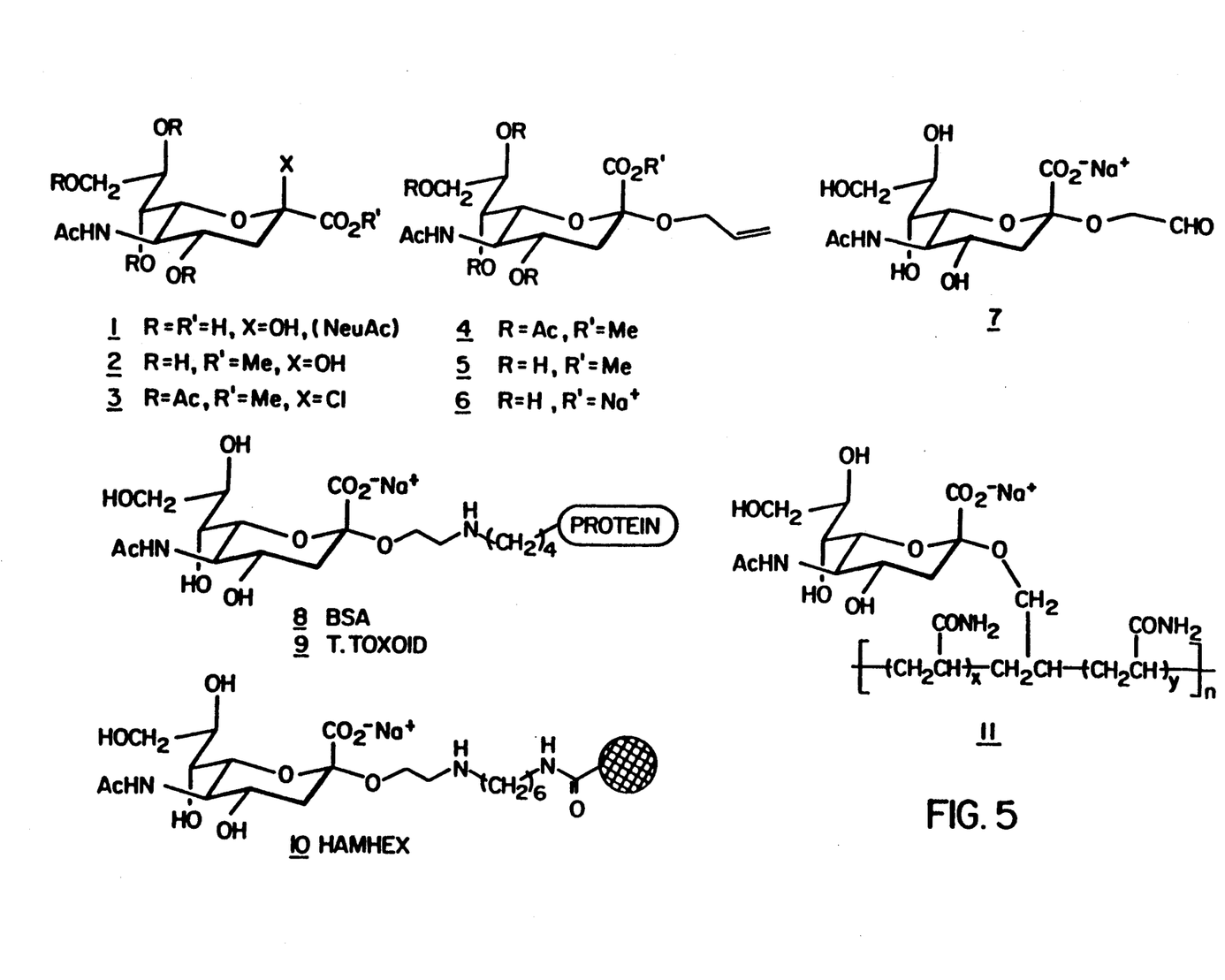
FIG. 5 shows a scheme for the production of sialic acid conjugates listing intermediates.
Figure 6:
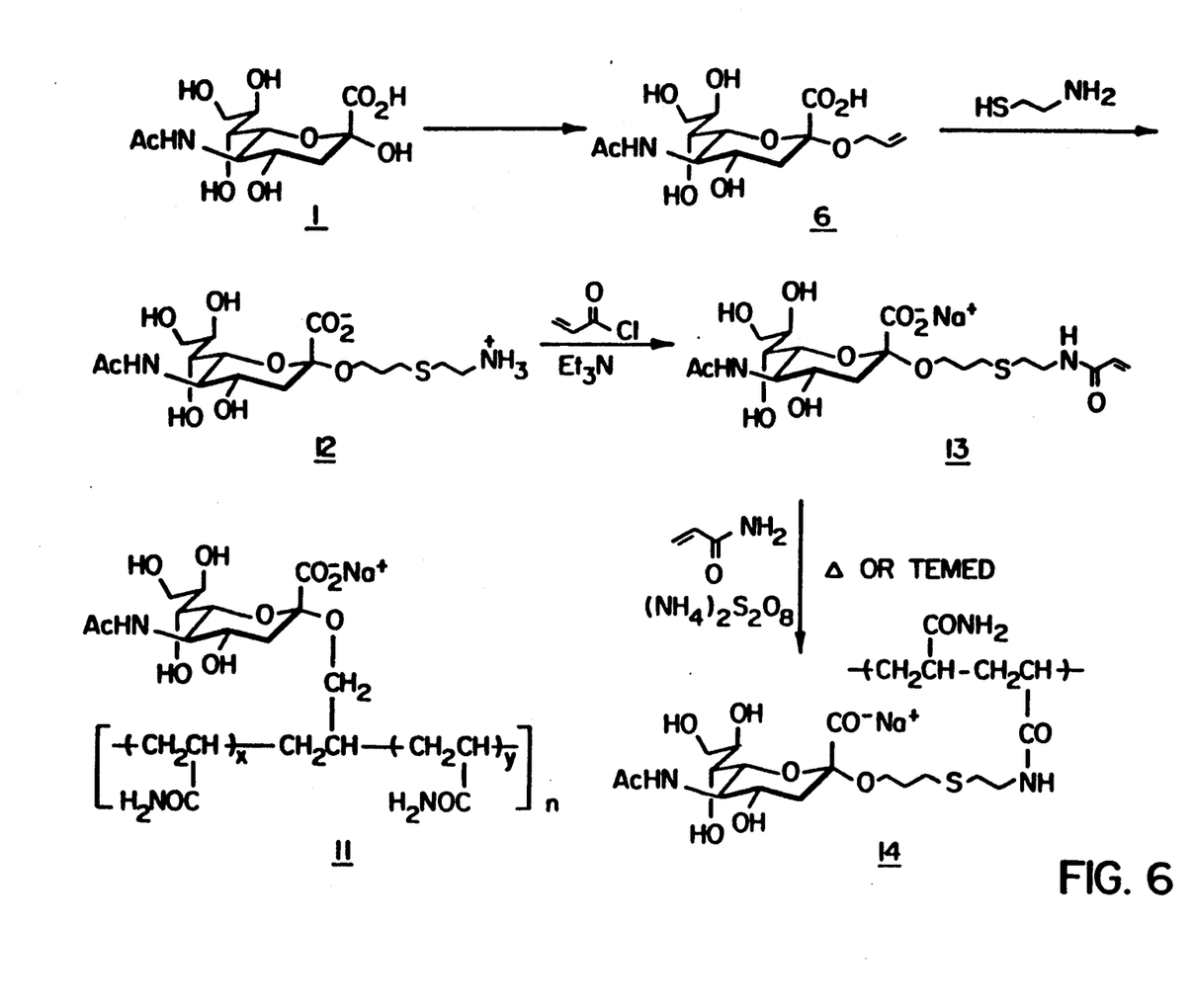
FIG. 6 shows a scheme for the production of sialic acid conjugates having spacer arms of a length which give improved immunochemical properties.
Figure 7:
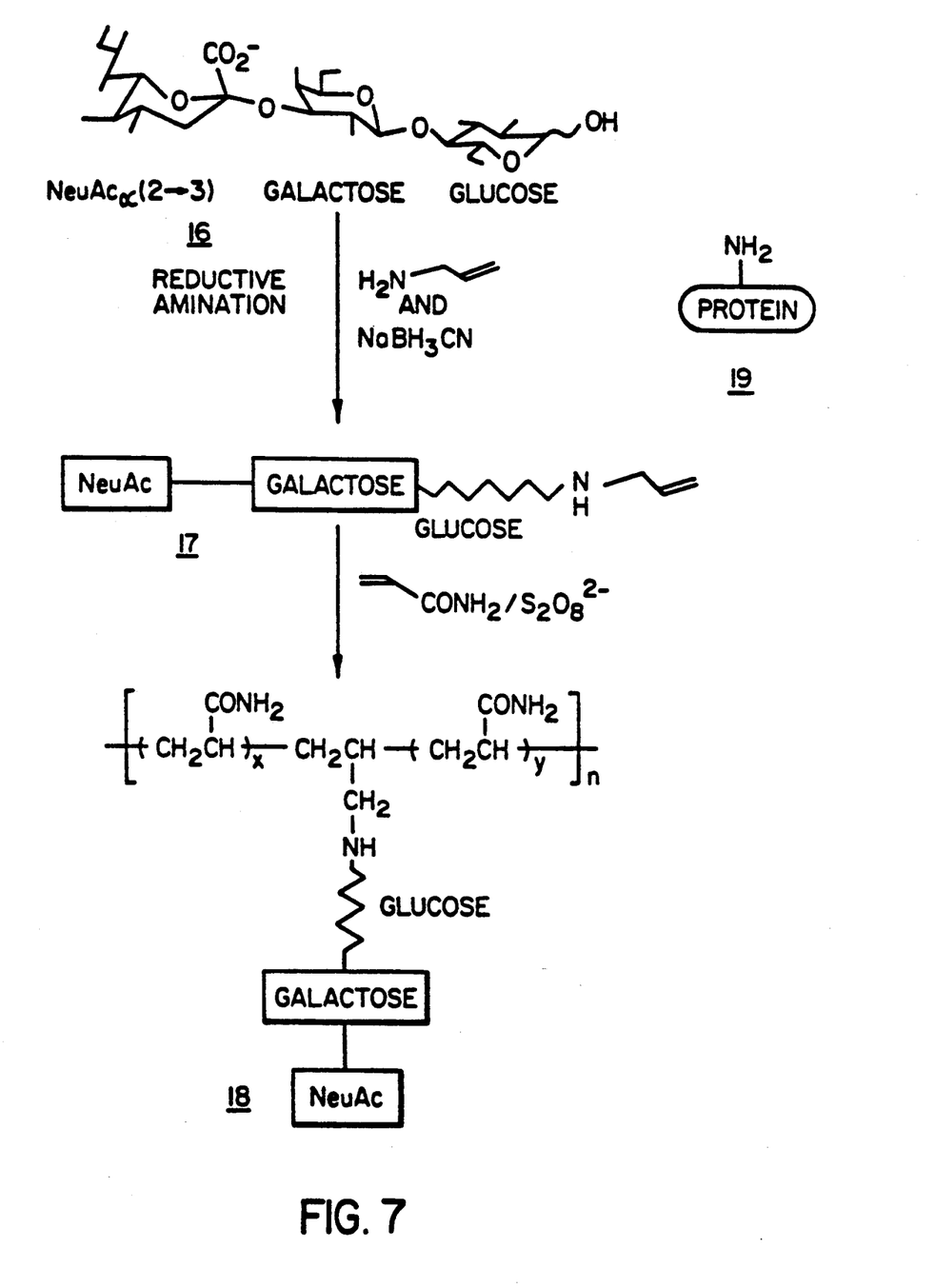
FIG. 7 shows a scheme for the production of disaccharide conjugates containing NeuAc.
Figure 8:
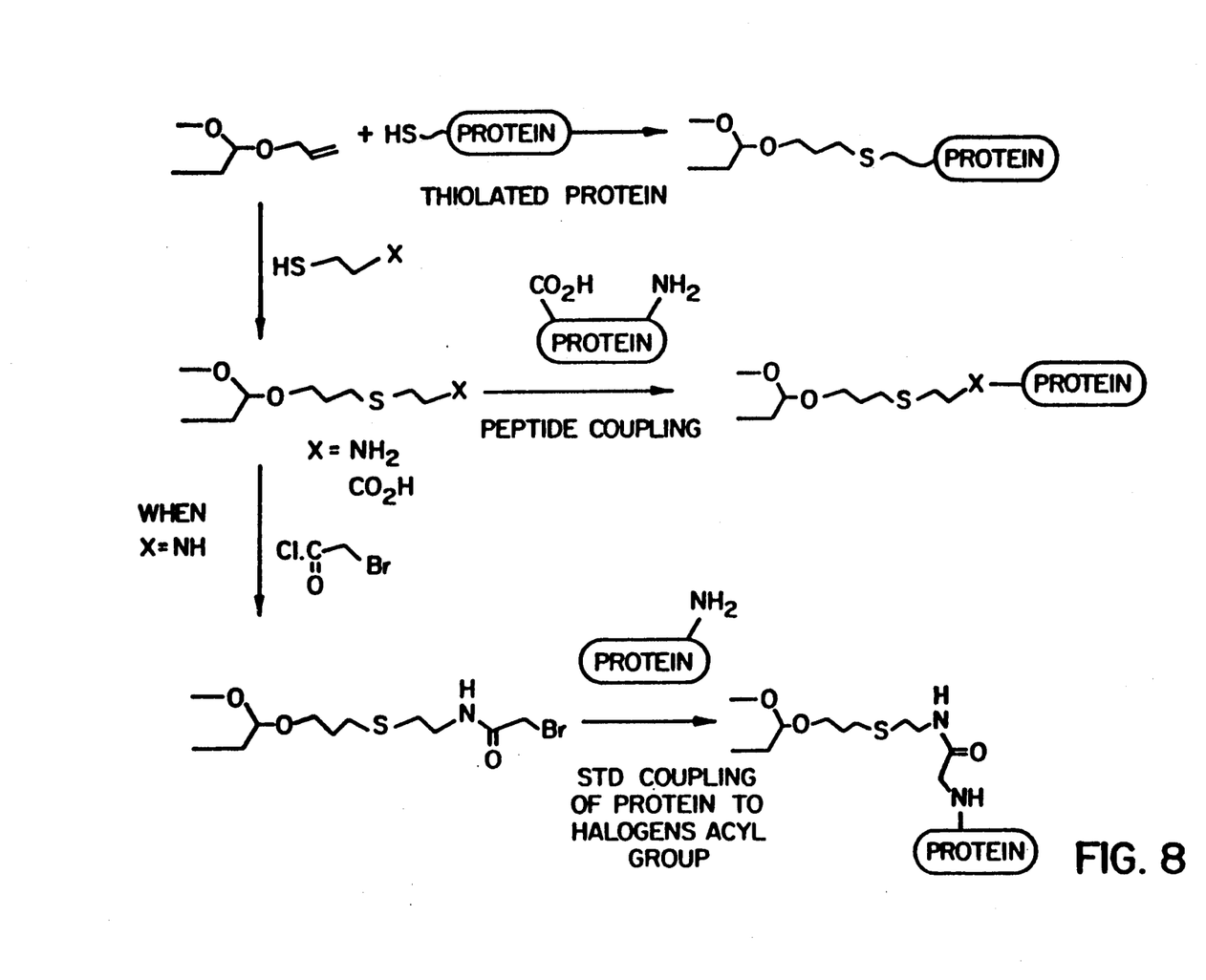
FIG. 8 shows schemes for production of conjugates linked to modified proteins, conjugates containing peptide links and conjugates created by coupling of proteins to halogenoacyl groups.

Compounds 6 and onwards shown in the schemes are new and compound 6 or an olefinic analogue thereof comprises a chemical starting point for many of the faulty compounds produced by the invention.

The coupling means is usually a spacer and a $C_2$ to $C_{10}$ olefinic spacer is to be preferred, an allyl spacer of the type shown in compound 6 is especially preferred. Other spacer moieties which have proved useful include adipic acid dihydrazide $H_2N \cdot NH \cdot CO \cdot (CH_2)_4 \cdot CO \cdot NH \cdot NH_2$) and hexanediamine ($H_2N \cdot (CH_2)_6 \cdot NH_2$). These last two can be coupled onto a suitable protein as a carrier so that all that is required of the sialic acid based compound is that it has coupling means to link it to such a carrier.

By coupling means we mean to include a spacer in combination with the sialic acid, sialic acid derivative or oligosaccharide terminating in a sialic acid or sialic acid derivative, if multibranched at the end of at least the largest branch. Whether the spacer is physically linked to the moiety X or the carrier is not as important as the combination of the elements.

As can be seen in the examples below the spacer whereby an antibody can be raised to the sialic acid based moiety may prior to coupling to the carrier, be present or be built up on the carrier. This is especially the case if the carrier is a protein, many proteins can be modified, by thiolation for example, to be made into suitable reactants.

The proteins which can be used as carriers to the sialic acid-type oligosaccharides of the invention can be synthetic or natural of a type usually used for preparing antigens such as serum albumin, serum globulin, thyroglobulin, hemoglobulin, polylysine, etc.

Antibodies are raised to the sialic acid-type oligosaccharides of the invention in the usual manner by administering the antigen to a mammal, such as a rabbit, and collecting antibody produced by the animal. A predetermined amount of the antigen is diluted to a suitable concentration with, for example, physiological saline, and Freund's adjuvant added and the resulting composition administered in the usual manner, preferably subcutaneously.

A standard method of raising the antibodies is as follows:

Complete Freund's adjuvant (1 ml) containing 0.4 mg of the sialic acid-type antigen 8 (for instance the product obtained in Example III) is injected into the footpads of a New Zealand white rabbit. Three weeks thereafter, the same amount of complete Freund's adjuvant containing the antigen 8 is injected. This procedure is repeated every 2 weeks 3 times. Ten days after the last injection, the blood is collected from the test animal and centrifuged to collect antiserum and obtain the desired anti bodies. The antibodies may be stored at $-70°$ C. The antiserum may also be freeze-dried to obtain the antibodies in a dry form.

As an alternative monoclonal antibodies can be produced by isolating spleen cells from an animal which has been treated with the compounds according to the invention as antigens and subsequently fusing such spleen cells with cancer cells and then separating and culturing the resulting hybridomas and selecting the cell lines that produce the antibodies of interest.

EXAMPLE I

Synthesis of Neoglycoproteins and Pseudopolysaccharides Containing N-acetylneuraminic Acid: a General Scheme Synthesis of the antigenic Allyl 5-Acetamido-3,5-dideoxy-α-D-glycero-D-galacto-2-nonulopyranosonate (Allyl α-NeuAc, 6).

NeuAc (1) was isolated in yields of 5–6% (by weight) from edible bird's nest according to literature procedure. The methyl ester of NeuAc (2) was obtained in quantitative yield by the method of Kuhn et al: mp 193.5°–194.7° C. (MeOH-Et$_2$O), $[\alpha]_D-28°$ (H$_2$O), reported mp 179°–180° C., $[\alpha]_D-28°$ (H$_2$O). The transformation of the ester 2 to the acetochloroneuraminic acid 3 was accomplished very efficiently through a procedure involving the treatment of 2 with acetyl chloride in the presence of dry acetic acid in a sealed reaction vessel at room temperature for 24 h. Co-evaporations of the reaction mixture with dry toluene afforded an almost quantitative yield of 3 (>93%, $^1$H NMR). The $^1$H NMR data were identical with published data in both CHCl$_3$ and C$_6$D$_6$. $[\alpha]_D-63°$ (CHCl$_3$).

The freshly prepared chloride 3 (2.40 g, 4.71 m mol) was dissolved in dry allyl alcohol (30 ml, dried over activated 4A molecular sieves). Silver salicylate (2.52 g, 10.29 mmol) and powdered molecular sieves 4Å (2 g) were then added and the reaction mixture was kept under argon and protected from light with aluminum foil at room temperature. After 2–3h, the solution was filtered through Celite which was washed with chloroform and was evaporated under vacuum to dryness. The yellow syrup was dissolved in chloroform and the organic phase was successively washed with an equal volume of a saturated aqueous solution of sodium bicarbonate, 10% w/v sodium thiosulfate and water. The organic phase was dried over sodium sulfate and after filtration, evaporated to dryness to give 2.35 g (4.43 mmol) of 4 as a syrup (94%). A sample was crystallized in methanol-ether-hexane to give 4 mp 153.6°–155.7° C., $[\alpha]_D-14.2°$ (CHCl$_3$). These physical data agreed well with those of the compound previously prepared by Eschenfelder and Brossmer using polymeric silver catalyst Zemplen deacetylation of 4 (30 ml methanol, 1 ml 1M sodium methoxide in methanol, pH 8.5) gave a quantitative yield of 5. A sample of 5 crystallized in methanol-ether had mp 143°–144° C., $[\alpha]_D-10.1°$ (c=0.95, methanol). Analysis, Calc. for C$_{15}$H$_{25}$NO$_9$: C, 49.58; H, 6.94; N, 3.86. Found: C, 49.74; H, 7.04; N, 3.73.

The α-allyl glycoside methyl ester 5 (2.15 g, 5.94 mmol) was treated for 3 h at room temperature in 0.1M aqueous sodium hydroxide (50 ml). The reaction mixture was then cooled and neutralized with REXYN 101 (H+) resin (pH reached 2). The solution was filtered, neutralized to pH 7.0 with 0.1M sodium hydroxide and lyophilized. The yield of the white powder 6 was 2.12 g (5.72 mmol, 96% yield) with mp. 245°–250° (dec), $[\alpha]_D-9.1°$ (c=0.66, water). The $^{13}$C-NMR spectral data of 5 and 6 are given in the Table I below.

EXAMPLE II

Preparation of the Antigenic Aldehyde-Glycoside NeuAc7.

The allyl glycoside 6 (1.0 g, 2.70 mmol) was dissolved in 50 ml of methanol. The solution was cooled to $-78°$, purged with oxygen for 5 min and treated with ozone till the solution remained blue. After 10 min, the ozone was evacuated with nitrogen for 15 min and while at $-78°$, 0.5 ml of dimethylsulfide was added. The resulting solution was allowed to warm to room temperature over a period of an hour. The clear solution was then evaporated to dryness to give I (1.0 g, quantitative) homogeneous by 1c R$_f$0.58, ethyl acetate: isopropanol: water, 3:2:2 v/v/v $[\alpha]_D-1.8°$ (0.1M pyridiniumacetate pH 5.0).

Analysis, Calc. for C$_{14}$H$_{22}$NNaO$_9$·H$_2$O: C, 43.15, H, 6.16; N, 3.60. Found : C, 43.87, H, 5.66 ; N, 3.93. The $^{13}$C-NMR spectral data of I are given in the Table I below. The $^1$H-NMR in D$_2$O shows δ(ppm) : 1.70 (dd,1H,H$_{3ax}$), 2.03 (s,3H,NAc), 2.73 (dd,1H,H$_{3eq}$), 3.42 (dd,2H,CH$_2$CHO), 5.11 (t,1H,hydrated CHO).

TABLE I $^{13}$C NMR CHEMICAL SHIFTS (ppm) of NEUAc DERIVATIVES

| Carbon | 5<br>α-OAll<br>CO$_2$Me | 6<br>α-OAll<br>CO$_2^-$Na$^+$ | 7<br>α-OCH$_2$CHO<br>CO$_2^-$Na$^+$ | 12<br>α-OCH$_2$CH$_2$CH$_2$<br>SCH$_2$CH$_2$NH$_3$<br>CO$_2^-$  $^+$ |
|---|---|---|---|---|
| 1 | 171.2 | 174.6 | 174.6 | 174.6 |
| 2 | 100.0 | 101.8 | 101.7 | 101.7 |
| 3 | 40.6 | 41.7 | 41.3 | 41.4 |
| 4 | 68.3 | 69.4 | 69.4 | 69.3 |
| 5 | 53.0 | 53.1 | 53.1 | 53.0 |
| 6 | 74.1 | 73.9 | 73.8 | 73.7 |
| 7 | 69.5 | 69.4 | 69.4 | 69.3 |
| 8 | 71.8 | 72.9 | 72.9 | 72.9 |
| 9 | 64.3 | 63.8 | 63.9 | 63.7 |
| N—Ac | 23.3 | 23.3 | 23.3 | 23.1 |
| C=O | 176.1 | 176.3 | 176.3 | 176.2 |
| OCH$_2$ | 67.0 | 67.1 | 68.2 | 64.1[b] |
| —CH= | 119.7 | 119.4 | — | 39.4,29.9 |
| =CH$_2$ | 134.3 | 135.0 | — | 29.3,28,3 |
| CO$_2$Me | 54.6 | — | — | — |
| CHO | — | — | — | — |

αSpectra taken on Varian CFT-20 in D$_2$O at 100 mg/ml relative to external TMS at 25° C. Spacer CH$_2$.

When the above ozonolysis conditions are performed on the ester 5, a quantitative yield of the methyl ester of 6 was obtained. It was used in the reductive amination coupling example X below to improve the extent of coupling. The following physical data for the methyl ester of 6 was obtained. (α)D−10.3° (0.1M pyridinium acetate pH 5.0). FAB MS gave an (M+1)$^+$ion at 366 consistent with $C_{14}H_{23}NO_{10}$. $^1H$—and $^{13}C$-NMR spectral data are the same as the above derivative 6 except for the added methyl ester protons and carbon which are 3.87 ppm ($^1H$) and at 54.6 ppm ($^{13}C$) respectively. The ring carbons of the methyl ester of 6 are similar to those of 5 (see Table I).

EXAMPLE III

Synthesis of the Antigenic/Immunogenic Sialic and -Protein conjugate 8, 8A, 8B, and 9

The direct coupling of the antigenic aldehydo NeuAc derivative 7 was efficiently effected by the in situ reduction of the imine initially produced. Although this procedure has been available for some time, the present description is the first one of a sialic acid which moreover, by virtue of its anionic character reveals facts never mentioned previously. Indeed, the build up of anionic charges on the protein carriers slows and even prevents the accumulation of too many sialic acid residues on the neoglycoproteins. This phenomenon tends to create a polyelectrolyte and maximizes to 20-25 the number of sialic acid residues incorporated. This situation could be obviated, if a greater incorporation is required, by performing the coupling with the carboxylate group of NeuAc 7 protected as the methyl ester 16. See the example X shown below.

The proteins used here represent a typical example of four different kinds of protein carriers. The first one used in the present example is the case of a native protein (for 8) bovine serum albumin (BSA), the second and third ones are characteristic of pre-modified proteins on which were coupled amino (for 8A) and hydrazido (for 8B) spacer corresponding to hexanediamine and adipic acid dihydrazide respectively. These spacers were introduced by standard carbodiimide coupling using a water soluble reagent 1-(3-dimethylaminopropyl)-3-ethyl carbodiimide hydrochloride (EDC). The extent of modification could be controlled by the stoichiometry of the reactant used and by the time required for the coupling. The fourth example represents the case of a human compatible protein carrier already in use for human vaccination. Thus, tetanus toxoid is a pre-modified protein obtained by formulation and is of common use. Our coupling methodology shows that it can also be used. However, the extent of the antigenic sialic acid incorporation was lower because there is less intact amino groups available for the reductive amination.

A representative example is as follows:

The sodium salt of the antigenic sialic acid aldehydo derivative 7 (20 mg, 54 μmols), bovine serum albumine (BSA, Sigma, 12 mg, 0.18 μmol) and sodium cyanoborohydride (NaBH$_3$CN, Aldrich Co., 17 mg, 290 μmols) were dissolved in 0.2M sodium phosphate buffer pH7.0 (2.5 ml). A drop of toluene was added to prevent bacterial growth. The solution was stirred for three days at 37° after which time the excess hydride reagent was destroyed by lowering the pH to 5.0 with few drops of acetic acid. The reaction mixture was then transferred into a dialysis bag (M.W. cut off 12-14 kDa) and was exhaustively dialyzed against distilled water for two days. The content of the bag was freezedried. The extent of sialic acid incorporation was estimated by the resorcinol method of Svennerholm. The protein content was measured by the Lowry method and therefore the number of sialic acid residues for each molecule of protein carrier was 23. This number did not change after size extrusion chromatography on Sephadex® G-50 in water. These results demonstrate the covalent nature of the bond between sialic acid and the protein linked at the ε-amino groups of the lysine residues (amino acid analysis). The number of sialic residues on both the amino and hydrazide derivatives of BSA 8A and 8B were 7.5% (w/w) and 12.2% (w/w) respectively. These values correspond to ~20 NeuAc residues per protein molecule. In the case of the tetanus toxoid conjugate 9, the incorporation was 10 NeuAc residues.

At this point many attempts were tried to increase the level of incorporation of NeuAc residues. The effects of temperature, buffer pH, time, co-solvent, molar ratio of the reagents were all evaluated. However only marginal differences in the level of NeuAc incorporation were observed. This was attributed to the charge repulsion phenomenon described above and the problem was solved in the example X given below.

EXAMPLE IV

Synthesis of Sialic Acid Immunoadsorbent 10

The example given below shows the coupling of an aldehyde form of NeuAc (7) to aminated particles. These particles can successfully be used as immunoadsorbents for affinity chromatography, complement fixation and for agglutination studies when the particles are ~1 μm in diameters.

Aminated human albumin microspheres (<10 μm; 3M Co., Minnesota; 30 mg; 0.44 μmol) obtained by coupling 1,6-hexanediamine to the commercial beads with EDC were allowed to swell for 6 hr at room temperature. The appropriate swelling system was a solution (10 ml) of 0.2M sodium phosphate buffer pH 7.0 containing the detergent (Pluronic® F.68, 1 mg, 0.025% solution). The sodium salt of aldehyde 7 (68 mg, 174 μmols) and NaBH$_3$CN (40 mg, 640 μmols) were then added and the reaction mixture was stirred for 4 days at 37°. The modified beads 10 were recuperated by vacuum filtration with the aid of a fritted glass funnel (fine porosity) and successively washed with 0.5M sodium chloride, water and acetone (500 ml each). The yield of 10 was 21.4 mg, representing a 5.7% increase in weight. The content of sialic acid was estimated by the Svennerholm procedure.

EXAMPLE V

Synthesis of the sialic acid copolymer 11

The copolymerization of the olefinic residue of 6 with acrylamide proceeds by an electron transfer polymerization using the ammonium persulfate redox system. The initiation of the reaction was done with TEMED (method A) or by heat (method B).

A solution of allyl glycoside of NeuAc sodium salt (6, 200 mg), acrylamide (100 mg) and ammonium persulfate (10 mg) in distilled water (4 ml) was deaerated during 30 min. by using a water pump aspirator. The solution was divided into two equal fractions of 2 ml each. The first fraction was treated by method A. N,N,N',N'-tetramethylethylenediamine (TEMED, 50 μl) was added and the solution was stirred over night at room temperature and processed as below. The second fraction was treated by method B. The solution was heated for 5-10 min. on the boiling water bath. After cooling the two above preparations were independently dialyzed against distilled water and lyophilized. Method A gave 60 mg of copolymer 11 having a NeuAc content of 18-20% (w/w) based on the Svennerholm method. Method B gave 56 mg of copolymer 11 with a NeuAc content of 15% (w/w). Both copolymers gave a void volume peak on Sephadex® G-50 eluted with 0.5M pyridinium acetate buffer pH 5.4.

Size extrusion chromatography indicated a molecular weight of 50-70 kDa. The copolymers gave an immunodiffusion bands with wheat germ agglutinin (WGA) in agarose gel performed according to Ouchterlony. $^1$H-NMR showed a relative content of ~1 NeuAc residue for 18-20 acrylamide units. The same behaviour in the maximization in the NeuAc incorporations was also observed (see example III). This problem could also be eliminated by performing the polymerization with the ester allyl glycoside of NeuAc (5) (see example VIII).

The fact that the above protein conjugates (8-9) and this copolymer 11 proved useful in serological studies was ascertained by their use in an ELISA test performed in microtiter plates (Dynatech, U.K.). Standard ELISA technique performed with WGA-peroxidase conjugate (EY Co., California) indicated that the plates were efficiently coated with the sialic acid antigens mentioned above.

The $^1$H-NMR in 11 in D$_2$O showed broad polymer methine protons at 2.0-2.4 ppm and methylene protons at 1.0-1.8 ppm. The NeuAc protons remained virtually unchanged. The $^{13}$C-NMR of 11 showed the NeuAc carbons at the same chemical shifts (see Table I, 6, 1) with the added resonance originating from the acrylamide residues at 181.4 and 180.3 ppm (CONH2), at 43.2 ppm (CH) and at 36.2 ppm (CH2).

EXAMPLE VI

Synthesis of the Antigenic Sialic Acid 12 Having An Extended Amine Functionality Through Radical Thiol Addition The sodium salt of the allyl glycoside NeuAc 6 (293 mg, 0.80 mmol) and cysteamine hydrochloride (750 mg, 6.6 mmols) were dissolved in 4 ml absolute ethanol. The solution was then evaporated under vacuum. Water (2 ml) was added and the solution was deaerated for 30 min. under water aspirator. The reaction mixture was exposed to a UV light (254 nm) and stirred for 24 h at room temperature. At this point, the tlc on silica gel developed in ethyl acetate, acetic acid, water (3:2:1 v/v/v) indicated no remaining starting material and only one sugar component at Rf 0.15. The solution was then passed through a column (1.5×40 cm) of cation exchange resin DOWEX 50 W×0.8 in the ammonium form. The sialic acid containing fractions were pooled and freeze-dried. The residue (480 mg) was then passed on a Sephadex G-10 column which was eluted with water. The sialic acid containing fractions were again pooled to give the pure title compound 12 in 60% yield after lyophilization. Fast atom bombardment mass spectrometry (FAB MS) gave a (M+1)+ ion consistent with a M.W. of 426 for C$_{16}$H$_{30}$N$_2$O$_9$S. $[\alpha]_D$ −8.3° in 0.1M pyridinium acetater pH 5.0. The $^{13}$C-NMR data are included in Table I above $^1$H NMR in D$_2$O δ(ppm) relative to internal acetone at 2.225 ppm: 3.542-3.890(9H, NeuAc+OCH$_2$ spacer), 3.224(t, 2H, —CH$_2$NH$_2$, J=6.5 Hz), 2.857(t, 2H,k-SCH$_2$—, J=6.5 Hz), 2.748(dd, 1H, H$_{3eq}$, J$_{3ax,3eq}$=12 Hz, J$_{3eq,4}$=4.9 Hz), 2.658 (t, 2H, —CH$_2$S—, J=7.0 Hz), 2.030(s, 3H, NAc), 1.853 (q, 2H; OCH$_2$CH$_2$CH$_2$S; J=5.8 Hz), 1.651 (dd, 1H,H$_{3ax}$,J$_{3ax3eq}$=12 $\overline{Hz}$, J$_{3ax,4}$=12 Hz).

EXAMPLE VII

Transformation of the Antigenic Sialic Acid 12 Into the Acryloyl Comonomer 13

Compound 12 (14 mg, 33 µmols) was dissolved in 10 ml of methanol containing 10% triethylamine. The solution was cooled to 0° with an ice-bath. Acryloyl chloride as a 10% solution in dioxane (1 ml) was added portionwise over a period of 30 min. After an additional 30 min the solution was evaporated at 10° under high vacuum. The syrupy residue was purified by size extrusion chromatography on a column of Sephadex G-10 with water as the eluant. The sialic acid containing fractions, measured by the resorcinol colorimetric method, were pooled and freeze-dried to give 13 (14 mg, 29/µmols, 88%) as an homogeneous powder. TLC on silica gel Rf 0.36 with the above eluant (Example VI). $[\alpha]$D −11° in 0.1M pyridinium acetate pH 5.0. FAB MS gave an (M+1)+ion at 481 for C$_{19}$H$_{32}$N$_2$O$_{10}$S. $^1$H-NMR in D$_2$O δ(ppm): 6.282(dd, 1H, CH=CH$_2$, J$_{trans}$=17.0 Hz, J$_{gem}$=2.0 Hz), 5.766 (dd, 1$\overline{H}$, CH=CH$_2$, J$_{cis}$=9.6 hz, J$_{gem}$=2.0 Hz), 3.483(t, 2H, CH$_2$NH, J=$\overline{6}$.8 Hz), 2.748(dd, 1H, H$_{3eq}$, J$_{3ax,3eq}$=12 Hz, J$_{3eq,4}$=4.9 Hz), 2.744(t, 2H, SCH$_2$, J=6.6 Hz), 2.642(t, 2H, CH$_2$S, J=6.0 Hz), 2.030(s, 3H, NAc), 1.836 (q, 2H, OCH$_2$CH$_2$S, J=6.8 Hz), 1.645(dd, 1H, H$_{3ax}$, J$_{3ax,3eq}$=12 Hz,

EXAMPLE VIII

Synthesis of the Antigenic Sialic Acid Acryloyl Copolymer 14

The same electron transfer polymerization method described in Example V above was used. The added example shown here is included because it described the advantages of performing the polymerization with the NeuAc residues still protected as their methyl ester. The advantages being that higher incorporation of NeuAc were obtained. The removal of the ester protecting groups was efficiently done on the polymer itself without affecting its serological properties. Indeed, the two procedures gave the same copolymers 11 and 14 after deprotection.

Thus, the sodium salt of the acryloylated derivative 13 (18 mg), acrylamide (19 mg) and ammonium persulfate (2 mg) were treated as above in water (0.6 ml). TEMED (5 µl) was then added and the solution was stirred at room temperature overnight. After the above isolation procedure and lyophilization the copolymer 14 was obtained as a white fluffy powder (23 mg). The NeuAc content was measured (14% w/w). The M.W. was slightly above the one obtained previously (11) as compared by its relative mobility in agarose gel. The serological properties of this polymer are better than those of 11. This was estimated by its binding properties to both WGA and to the rabbit sera obtained against the antigenic sialic acid protein conjugates 8 and 9. These expected results are due to the presence of more accessible NeuAc residues on the spacer polymer 14 compared to the difficultly accessible ones in polymer 11. This constitutes a clear improvement over any known carbohydrate polymers.

The actual NeuAc contents of polymers 11 and 34 were raised by performing the above polymerizations with the corresponding monomer precursors having sialic acid residues Protected as their methyl esters 5 and methyl ester of 13. Repeating the above procedure gave copolymers with a NeuAc contents of as high as 35% (w/w). This represents one NeuAc residue per five acrylamide units. To compare their serological properties these esterified copolymers were treated with base under mild conditions to remove the methyl ester group in order to regenerate the intact copolymers 11 and 34.

Thus, 20 mg of the esterified polymer (11) was dissolved in 0.1M sodium hydroxide (10 ml). After 30 min. at room temperature the reaction mixture was neutralized to pH 7.0 with 0.1N hydrochloric acid (10 ml) and then transferred into dialysis tubing. Isolation of the polymer as described above gave 18 mg of (11).

EXAMPLE IX

Synthesis of the Antigenic Sialic Acid 15 Having An Amine Group

The actual methodology is based on a reductive amination reaction similar to the one used for the direct coupling of the aldehyde derivative 7 to proteins carriers to give neoglycoproteins 8–9. The fundamental difference here is reflected by the absence of positive charges in the vicinity of the antigenic sialic acid residues in the conjugate. Indeed, the covalent bond in the present case consists of an amide functionability introduced by using a water soluble carbodiimide in the coupling reaction.

Compound 1 (18 mg, 48 μM) was dissolved in 2 ml of a saturated solution of ammonium acetate in methanol. Sodium cyanoborohydride (10 mg, 238 μmols) was then added and the resulting solution was stirred at 60° for 24 h. After cooling, the excess hydride reagent was neutralized with glacial acetic acid to bring the pH to 5.0. After an hour at room temperature the solution was loaded on a column of Sephadex®G-10 (1.5×90 cm) and the compound was eluted with water. The sialic acid positive fractions (resorcinol) were pooled and lyophilized to give the antigenic amine derivative of sialic acid compound 15 (9.2 mg, 51%) Rf 0.17 in n-propanol-water 8:2(v/v). $[\alpha]_D -18.5°$ in 0.1M pipidinium acetate buffer pH 5.0 Rf 0.21 in ethyl acetate: acetic acid: water (3:2:1 v/v/v). $^1$H-NMR in $D_2O$ relative to acetone at 2.225 ppm: 1.73(dd,1H, $H_{3ax}$), 2.03 (s, 3H, NAc), 2.72 (dd, 1H,$H_{eq}$), 3.19 (t,2H, $\underline{CH_2}NH_2$), 3.96 (t, 2H, $O\underline{CH_2}$), 3.55–3.88 (7H, remaining NeuAc protons).

EXAMPLE X

Coupling of the Aldehydoester of 6 to Protein Carriers

The present example is essentially similar to the one described in Example III producing the same sialic acid conjugated proteins 8–9 with the basic difference that it permitted an higher incorporation of sialic acid residues on the protein. The reason for this is the consequence of coupling neutral sialic acid antigens to the proteins since its carboxyl group is protected as the methyl ester. Thus, in the present example, the methyl ester of 6 for which the synthesis is described in Example II above will be used in the direct coupling by reductive animation.

The aldehyde methyl ester derivative of 6 (22 mg, 60 μM), bovine serum albumin (10.4 mg, 0.16 μmol) and sodium cyanoborohydride (21.8 mg, 38 μmols) were dissolved in 0.2M sodium phosphate buffer pH 7.0 (3.3ml) containing methanol (30% v/v). Few drops of toluene were added and the solution was stirred for four days at 37°. After cooling to room temperature, glacial acetic acid was added to drop the pH to 5.0. The resulting solution was transferred into dialysis tubing and was dialyzed for three days against running tap water. The new conjugate 8 was purified on Sephadex® G-50 eluted with water. It has a sialic acid content of 53 residue per BSA molecule as determined by the resorcinol method for sialic acid and by the Lowry method for the protein.

EXAMPLE XI

Synthesis of the Copolymerizable Antigenic Sialyl oligosaccharide 17

In order to render even more immunospecific the sialic acid conjugates developed so far, we initiated the conjugation of the sialyl trisaccharide 16, namely sialyl $\alpha$(2–3)-lactose. This interesting trisaccharide could be obtained synthetically as described in the literature or by the preferred isolation methodology described here. The trisaccharide 16 has been isolated for many years from bovine colustrum by tedious anion exchange chromatography or more recently by HPLC chromatography. We decided to shorten the isolation procedure by exploiting the fact that the sialyl-$\alpha$-(2–3)-galactose moiety in the trisaccharide 16 is the principal constituent of the cow colustrum (400–500 mg/l) and also because it was prone to form an internal lactone. This lactone was formed between the carboxyl group of the sialic acid and the OH-2 group of the neighbouring galactose unit upon treatment with glacial acetic acid. The lactose formation permits to the trisaccharide 16 to become the only neutral sialyloligosaccharide species to be present in a crude sialyloligosaccharide mixture, therefore allowing it to be the only component not to be retained by the anion exchange column. This procedure gives rapidly a significant amount of the pure sialyl $\alpha$(2–3) lactose 16 useful in many of the configuration procedures described in the following example.

The fresh cow colustrum (4 1) was mixed and extracted with chloroform-methanol (3 1, 2:1, v/v) to remove residual lipid and to precipitate the proteins. The phases and the precipitate were separated by centrifugation at 5000 rpm for 15 min at 4° to give a yellowish aqueous phase 1 1 of which was then passed on an anionic exchange column (3.0×50 cm) of DOWEX 1×8 resin 200–400 mesh, acetate form). The neutral oligosaccharides (mainly lactose) were washed off the column with distilled water (~8 1). The crude monosialyloligosaccharides were then eluted all together with pyridimium acetate buffer (100 mM, 1 l, pH 5.0). The sialic acid containing fractions were pooled and freeze-dried to give ~0.80–1.0 g of crude oligosaccharides. At this stage, the crude mixture can be processed as described in the literature to obtain the individual monosialyloligosaccharides isomers. However, to fish out the $\alpha$(2→3) isomer 16, the mixture is treated with glacial acetic acid (100 ml) for five days. The solution is filtered and lyophilized. The white powder is then dissolved in 1 mM pyridinium acetate buffer pH 5.0 and passed through a short column (2.5×20 cm) of ammonium resin DOWEX 1°×8(acetate form) from which the compound 16 is the only component to be eluted with the same buffer. The sialic acid positive fractions (resorcinol) are pooled and freeze-dried to give the lactone of 16 (300 mg) which can be used directly in the next step since the lactone is very sensitive to hydrolysis and compound 16 obtained by the above procedure possesses all its physical dada ($[\alpha]D$, $^1$H— and $^{13}$C-NMR, TLC, FAB MS) in accordance with literature data.

Thus, the basic conditions used in the following reductive animation are sufficient to regenerate 16.

Compound 16 (65 mg) and allylamine (960 mg) were dissolved in methanol (4 ml). The pH was adjusted to 8.1 with glacial acetic acid followed by the addition of sodium cyanoborohydride (92 mg). The solution was refluxed for 5 h. After cooling the crude product was first obtained by precipitation from acetone and after filtration the above precipitation was done few times. A final purification of the white solid was done by size extrusion chromatography on Sephadex ® G-10 eluted with water to give pure 17 (30 mg, 46% not optimized). The Rf of pure 17 is 0.44 in n-propanol water, ammonium hydroxide (6:2:1). $[\alpha]_D - 1.5°$ in 0.1M pipidinium acetate pH 5.0). $^1$H-NMR in D$_2$O: 1.80 (dd, 1H, H$_{3ax}$), 2.03 (s,3H, NAc), 2.76 (dd, 1H, H$_{3eq}$), 4.60 (d, 1H, H1-Gal), 5.52 and 5.90 (3H, olefinic hydrogens). It is to be noted that the anomeric proton of the glucose residue did no longer appear at the usual low field chemical shift.

EXAMPLE XII

Synthesis of the Sialyloligosaccharide Copolymer 18

The polymerization of the olefinic sialyl α[2-3]lactose trisaccharide 17 in which the glucose residue has been destroyed as an immunogenic entity was effected by a similar electron transfer process described above in the Example V.

A solution of compound 17 (13 mg), acrylamide (12.4 mg) and ammonium persulfate (2 mg) in water (0.5 ml) was treated under vacuum (water aspirator) for 30 min to remove dissolved oxygen. TEMED (10 μl) was then added to initiate the copolymerization which was pursued for 16 h at room temperature. The reaction mixture was then exhaustively dialyzed against distilled water for 3 days. The obtained copolymer 18 (11.5 mg) was isolated as a white powder by lyophilization. The average molecular weight of 18 is also in the 50 kDa range as judged by its relative mobility in double agar immunodiffusion. Its sialic acid content was 8.6% by weight (resorcinol method) and this value was identical to the galactose content as determined by the phenol-sulfuric acid method. These results confirmed that the allylamine moiety introduced on the trisaccharide was an efficient comonomer in the above copolymerization procedure and that this methodology was mild enough to preserve the acid labile linkage of the sialyloligosaccharide.

The antigenicity of the above mentioned sialyl-galactose copolymer 18 was demonstrated by its capacity to bind to WGA and to the rabbit antibodies raised against the sialic acid protein conjugates 8 and 9. Indeed, double radial immunodiffusion in agarose and quantitative precipitine experiments gave indicative results.

EXAMPLE XIII

Direct Coupling of the Sialyl Oligosaccharide 16 to Protein Carriers. Preparation of the BSA Conjugate 19

The direct coupling of 16 to BSA follows a methodology previously described for the coupling of 7 to BSA (see Example III). However, in the present case, the procedure takes advantages of the fact that the aldehyde group to be coupled to the ε-amino group of the lysine residues of BSA are integral constituent of the reducing aldose residue (glucose). We previously demonstrated that in a similar situation where sialic acid was absent, a sodium borate buffer had illustrated distinct raised in the kinetics of conjugation. Therefore, the conditions described below were chosen to make the reaction complete within a day rather than a two weeks time reported previously. However, the negative charge effect reported above again limited to 20–25 the number of sialic acid residues that could be incorporated.

Compound 16 (10.4 mg), BSA (10.7 mg) and sodium cyanoborohydride (26 mg) were dissolved in 0.2 M sodium borate buffer pH 8.7 (1.5 ml). The solution was heated to 55° (oil bath) and stirred for 24 h. After exhaustive dialysis and freeze-drying the sialyl α(2–3)-lactose-BSA conjugate 19 (1.3 mg) was obtained as a white powder. The sialic acid content was 24 moles per mole BSA. This number remained after size extrusion chromatography on Sephadex ® G-50 in water showing that covalent linkage had occurred.

The antigenicity of this material was the same with the above criteria as the copolymer 18 described in Example XII.

What we claim as our invention is:

1. A multicomponent kit for detecting a sialic acid-containing antigen in a sample which kit comprises at least first and second components are in separate containers, said first component comprising an antibody which selectively binds to a compound having a terminal sialic acid moiety, said compound having the formula wherein each R separately represents hydrogen or acetyl,

R$^1$ represents hydrogen, methyl, sodium or potassium;

R$^2$ represents hydrogen, acetyl or hydroxyacetyl; each (sugar) represents a sugar moiety selected from the group consisting of galactose, glucose and lactose;

n is 0, 1 or 2,

A represents a heteroatom selected from the group consisting of oxygen, sulphur, and nitrogen and stands for or replaces an oxygen atom at the reducing end of the sugar moiety or sialic acid moiety; and W' represents —CH$_2$CH$_2$CH$_2$—S—CH$_2$CH$_2$NH-COCH$_2$CH$_2$—, —CH$_2$—CH$_2$—, —CH$_2$CH$_2$C-H$_2$—S—CH$_2$CH$_2$NH—, or —CH$_2$CH$_2$CH$_2$—S—CH$_2$CH$_2$NHCOCH$_2$—; and C constitutes a carrier, said second component comprising detection means for detecting a reaction between said antibody and said compound.

2. A kit according to claim 1 wherein said antibody is adsorbed onto a solid substrate.

* * * * *

UNITED STATES PATENT AND TRADEMARK OFFICE
CERTIFICATE OF CORRECTION

PATENT NO. : 5,192,661
DATED : March 9, 1993
INVENTOR(S) : Rene Roy et al It is certified that error appears in the above-identified patent and that said Letters Patent is hereby corrected as shown below:

Column 1, line 42, after "response" insert --.--

Column 1, line 50, "cellcell" should be --cell-cell--

Column 6, line 33, "C,43.15" should be --C,43.1$_5$--

Column 6, line 41, Table I - Title "C NMR" should be --$^{13}$C NMR--

Column 9, line 31, "(CONH2) should be --(CONH$_2$)--

Column 10, line 28, after "12 Hz," insert
  --J$_{3ax,4}$ = 12 Hz), remaining H at 3.54-3.90(9H).--

Column 10, line 66, "Protected" should be --protected--

Column 11, line 62, "38 µmols" should be --380 µmols--

Signed and Sealed this

Eighth Day of February, 1994

*Attest:*

BRUCE LEHMAN

*Attesting Officer*   *Commissioner of Patents and Trademarks*